US00PP11549P

United States Patent [19]

Cosner et al.

[11] Patent Number: Plant 11,549

[45] Date of Patent: Oct. 3, 2000

[54] IMPATIENS PLANT NAMED 'NEON SALMON'

[76] Inventors: Harlan Brian Cosner; Susan Lynn Cosner, both of P.O. Box 173, Broadbent, Oreg. 97414

[21] Appl. No.: 09/084,053

[22] Filed: May 22, 1998

[51] Int. Cl.[7] ..... A01H 5/00

[52] U.S. Cl. ..... Plt./317

[58] Field of Search ..... Plt./317

[56] References Cited

U.S. PATENT DOCUMENTS

P.P. 9,691 11/1996 Leue ..... Plt./317

*Primary Examiner*—Howard J. Locker

*Assistant Examiner*—Kent L. Bell

[57] ABSTRACT

A new and distinct cultivar of double flowered *Impatiens walleriana* plant named 'Neon Salmon', characterized by its large iridescent salmon flowers which are held above or beyond the foliage; consistently double and symmetrical flower form; numerous flowers per plant; freely and continuously flowering; freely branching, dense growth habit; upright mounded plant habit, globular to triangular in shape; having shiny dark green foliage with reddish blotches on the underside.

3 Drawing Sheets

The invention described in this application is a new and distinct cultivar of double flowered impatiens plant, botanically known as *Impatiens walleriana,* which shall be hereinafter referred to by its cultivar name of 'Neon Salmon'.

The new cultivar is a seedling of unknown parentage discovered growing in our Coquille, Oreg., breeding area. The new cultivar was found among a grorup of seedlings from random crosses made by us in our breeding program. The new cultivar was discovered on Jul. 15, 1995. Asexual reproduction of the cultivar by lateral stem cuttings at Coquille, Oreg. has shown the uniqueness of this new cultivar to be stable, and that it reproduces true to type in successive generations of asexual reproduction.

The traits which have been observed in successive generations which are unique to 'Neon Salmon', either in combination, or separately are:

1. Large, iridescent salmon colored flowers.
2. Flowers positioned above or beyond the foliage.
3. Consistently double, well shaped flowers.
4. Dark green foliage with reddish blotches on the underside of the leaves, and a shiny luster on the upper surface.
5. Numerous flowers per plant.
6. Reddish markings on the stems.
7. Strong stems and peduncles.

'Neon Salmon' can be compared to the Impatiens cultivar 'Salmon Sunrise' (U.S. Plant Pat. No. 9,691), marketed as 'Fiesta Salmon Sunrise'. In side by side comparisons, under commercial conditions, 'Neon Salmon' differed from 'Salmon Sunrise' as follows:

1. 'Neon Salmon' tolerated higher light levels than 'Salmon Sunrise'.
2. 'Neon Salmon' is more vigorous than 'Salmon Sunrise'.
3. 'Neon Salmon' does not spread or fall down in rains like 'Salmon Sunrise' due to stronger stems.
4. Flowers of 'Neon Salmon' are deeper and more iridescent in color than that of 'Salmon Sunrise'.
5. The underside of the leaves of 'Neon Salmon' have reddish blotches compared to solid coloring on the underside of the leaves of 'Salmon Sunrise'.
6. 'Neon Salmon' has wider foliage than 'Salmon Sunrise'.
7. The foliage of 'Neon Salmon' is darker than the foliage of 'Salmon Sunrise'.
8. The upper surface of the foliage of 'Neon Salmon' has a satiny, or pearly luster, compared to the relatively flat lusterless upper surface of 'Salmon Sunrise'.

A detailed comparison of 'Neon Salmon' and 'Salmon Sunrise' is set forth in Chart A at the end of the specification.

'Neon Salmon' has not been observed in all possible environmental conditions. Variations in fertility, climate, light quality and/or level, soil type, and temperature may cause phenotype variations, without genotype variations.

The accompanying drawing sheets utilize color photographs to illustrate the uniqueness of the new cultivar. The coloration of the photographs may not be entirely accurate due to light reflectance, or the amount of either red or blue light captured by the film. In the event there are differences between the written description and the color in the photographs, the written description shall control.

The photograph on the first sheet depicts a side view of 'Neon Salmon'.

The photograph on the second sheet depicts a side view comparison between 'Neon Salmon', left side, and 'Salmon Sunrise', right side.

The photograph on the third sheet depicts a comparison between the flowers, stems, and foliage of 'Neon Salmon' and 'Salmon Sunrise'.

The following observations, measurements, values, and comparisons describe plants grown in Coquille, Oreg., under the following cultural conditions:

1. Soilless medium.
2. High nitrate fertility plus trace elements.
3. Light levels of 3,000 to 7.500 foot candles.
4. Greenhouse covering of double layer polyethylene.
5. Day temperature ranging from 70° F. to 85° F.
6. Night temperatures ranging from 55° F. to 60° F.
7. Four inch Azalea pots were used.
8. Comparisons were made in late October.

In the following detailed description of 'Neon Salmon', all color references are made to The Royal Horticultural Society Colour Chart except where terms of ordinary usage and dictionary meaning are used.

DETAILED PLANT DESCRIPTION

Cultivar name: 'Neon Salmon', marketed as 'Tioga Neon Salmon'.

Botanical classification: *Impatiens walleriana.*

Parentage: Unknown.

Propagation:

*a*) *Type of cuttings*.—Terminal or lateral stems with leaves.

*b*) *Time to initiate roots*.—About 14 days at soil temperature of 72° F.

Roots: Numerous, well branched, fibrous in type.

Plant form: Upright mounded, globular to triangular depending upon cultural practices such as pinching and fertility.

Growth habit: Medium vigorous, dense, bushy, and self branching.

Plant height: About 18 cm.

Branching habit: Freely branching, numerous and strong. Number depends upon cultural practices, age of cuttings, and number of vegetative growth buds present on cuttings at time of propagation.

Stems: Size varies with age and cultural practices.

*a*) *Length*.—About 12 cm.

*b*) *Diameter*.—About 0.6 cm.

*c*) *Internode length*.—About 3.5 cm.

*d*) *Color*.—Close to 146B with markings close to 187B in internodes, more pronounced at node end.

Foliage: Leaves are simple, generally symmetrical, abundant, alternate, and flat.

*a*) *Size of largest*.—About 5.5 cm. long and 4 cm. wide.

*b*) *Shape*.—Ovate with acuminate apex, attenuate base, and crenate margin.

*c*) *Texture*.—Smooth.

*d*) *Color*.—Abaxial or bottom — 147B with blotching close to 183D with greenish overtones.

*e*) *Color*.—Adaxial or top — 147A with satiny or pearly luster.

*f*) *Color*.—Abaxial or bottom venation — close to 148A.

*g*) *Color*.—Adaxial or top venation — 146A, midrib 146A with very tiny spots close to 187A to 187B.

*h*) *Petiole*.—Length about 2 cm., about 3 mm. width, and about 2 mm deep. color — Close to 146B at base, reddish tinge close to 187B at node end.

Flower: Large and very iridescent salmon in color. Consistently double and symmetrical. Freely and continuously flowering. Flower buds open similar to a rose in fullness and shape. Flowers arise from leaf node upper or outer surface. About 12 flowers and/or buds are present on each lateral stem at any given time during the flowering season. Flowers are positioned above or beyond the foliage facing upwards or outwards and are self cleaning.

*a*) *Time to flower*.—Generally four to six weeks, but can vary with age and cultural practices.

*b*) *Season*.—Year-round under greenhouse conditions. In the garden continuous from Spring through Fall.

*c*) *Flower diameter*.—about 5.5 cm.

*d*) *Flower depth*.—About 2 cm.

*e*) *Bud length*.—About 0.8 cm.

*f*) *Bud diameter*.—About 0.6 cm.

*g*) *Bud shape*.—Ovate.

*h*) *Bud color before calyx begins to open*.—145A to 145B.

*i*) *Petal/petaloids*.—Numerous — generally 30 or more. Size of largest—Length about 2.1 cm. and width about 2.5 cm. Shape—Exaggerated obovate with rounded to emarginate apex, entire margin, obtuse to attenuate to truncate base. Texture—Satiny, smooth.

*j*) *Petal/petaloid color*.—Iridescent salmon color. Adaxial surface when opening—52A at edges, 40A from edges toward base with a basal spot of 61B. Mature—52A at edges, 40A from edges toward base with a basal spot of 61B, colors are slightly less vivid than when newly opened. Innermost petaloids are whitish in color. Abaxial surface when opening—52C. Mature—52C, innermost petaloids are whitish in color.

*k*) *Spur*.—Length — about 3.5 cm. Shape—curved acicular tube, largest at calyx. Color—close to 148A at base, with reddish tinge at tip.

*l*) *Calyx*.—measuring about 1 cm. wide and 1 cm. long. color—adaxial surface — close to but darker than 145A to 145B. abaxial surface—close to 145A to 145B. shape—ovate with cordate base, entire margin, and cuspidate apex.

*m*) *Peduncles*.—Length — about 2 cm. Diameter—about 2 mm. Strength—Moderate. Color—Between 146C and 146D. Angle—Upward or outward.

*n*) *Pedicels*.—Usually 2 or 3 per peduncle. Length—About 2 cm. Diameter—About 1.5 mm. Strength—Moderate Color—Between 146C and 146D.

Reproductive organs: Under optimal flowering conditions, none develop. Sterile petaloids develop in the place of the reproductive organs. 'Neon Salmon' is sterile and does not produce seed.

Disease resistance: Under commercial conditions, good resistance to botrytis has been noticed.

CHART A

| 'Neon Salmon' | | 'Salmon Sunrise' |
|---|---|---|
| Flower diameter - about 5.5 cm. | | about 4 cm. |
| depth - about 2 cm. | | about 1.25 cm. |
| Petal/petaloid mature color- | | |
| adaxial - | 52A at eges, 40A from edges toward base with a basal spot of 61B, colors are slightly less vivid than when newly opened. Innermost petaloids are whitish in color. | 52B |
| abaxial - | 52C, inner most petaloids are whitish in color. | 48D |
| Foliage - | length 5.5 cm.<br>width 4 cm. | 5.5 cm.<br>3.8 cm. |
| adaxial color - | 147A with satiny or pearly luster | 146A |
| abaxial color - | 147B with blotching close to 183D with greenish overtones | 147B |
| venation adaxial color - | 146A, midrib 146A with very tiny spots close to 187A to 187B. | 146A |
| venation abaxial color - | close to 148A | 147B |
| Stems - | length 12 cm.<br>diameter .6 cm | 12 cm.<br>.6 cm. |
| color - | 146B with markings close to 187B in internodes, being more pronounced at node end. | 146B |
| Petiole - | length about 2 cm.<br>width about 2 mm.<br>depth about 3 mm. | 1.5 cm.<br>2 mm. |
| color - | Close to 146B at base, with a reddish tinge at node end. | 146C |
| Spur - length - about 3.5 cm. | | 3 cm. |
| color - 148A at base, with reddish tinge at apex. | | 152D |
| Peduncle - length - about 2 cm. | | 2.25 cm. |
| diameter - about 2 mm. | | |
| color - between 146C and 146D. | | 144A |
| Pedicels - length - about 2.5 cm. | | 2.5 cm |
| color - between 146C and 146D. | | 144A. |

It is claimed:

1. A new and distinct cultivar of double flowered *Impatiens walleriana* plant as herein illustrated and described.

* * * * *

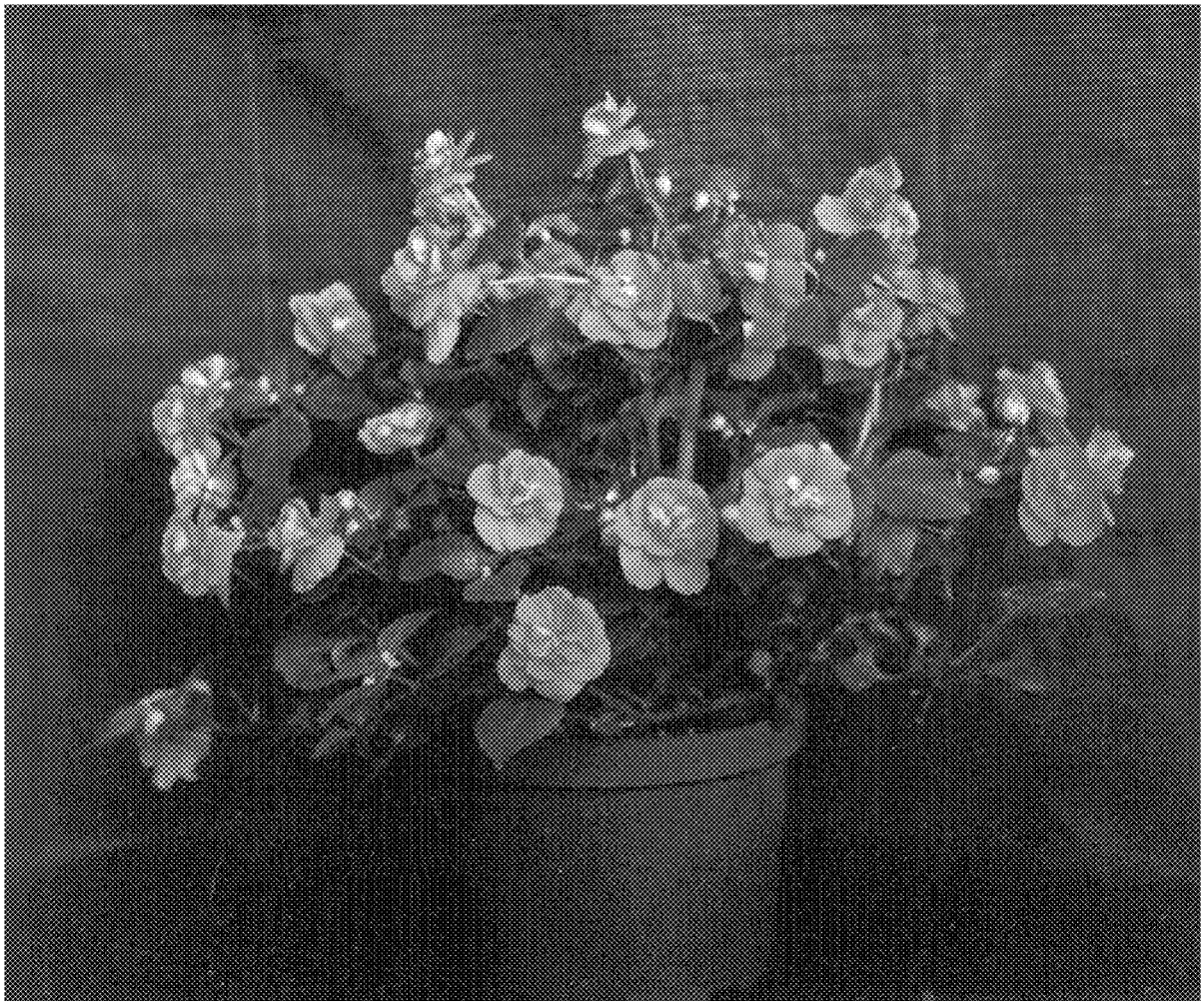

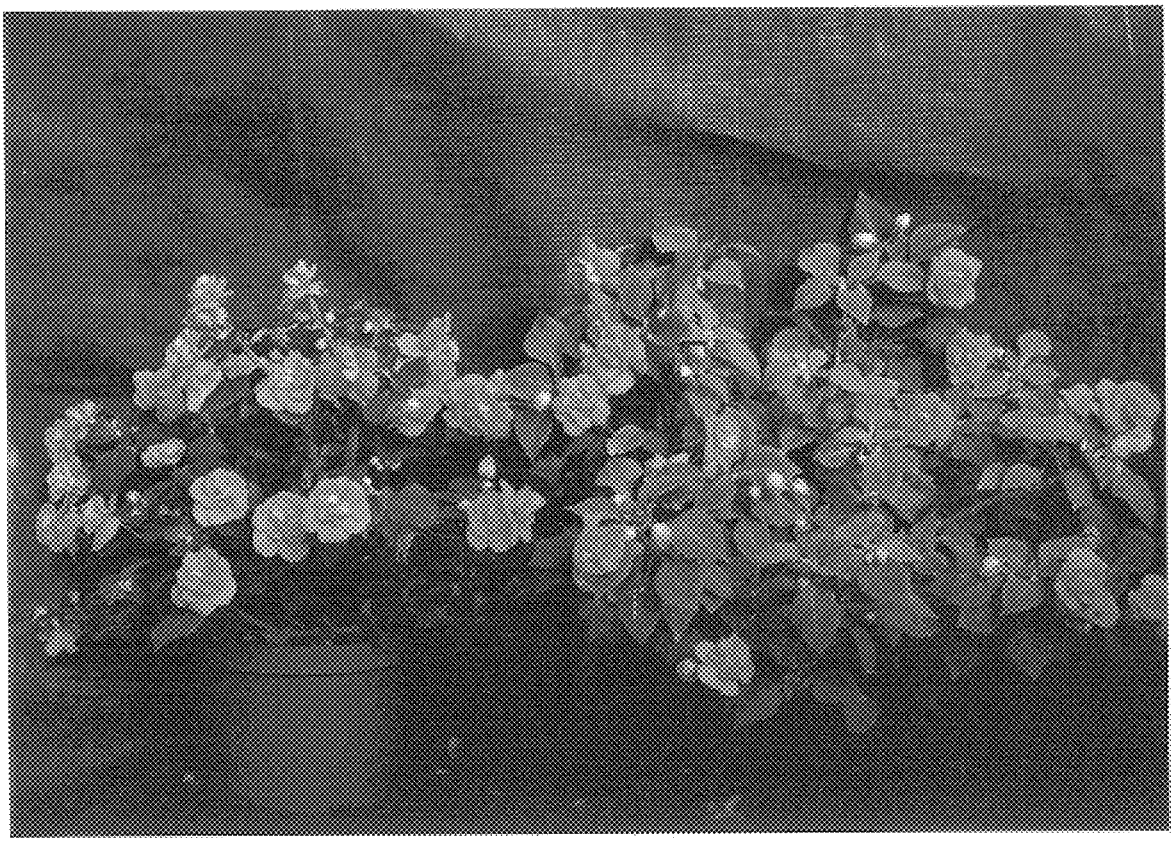

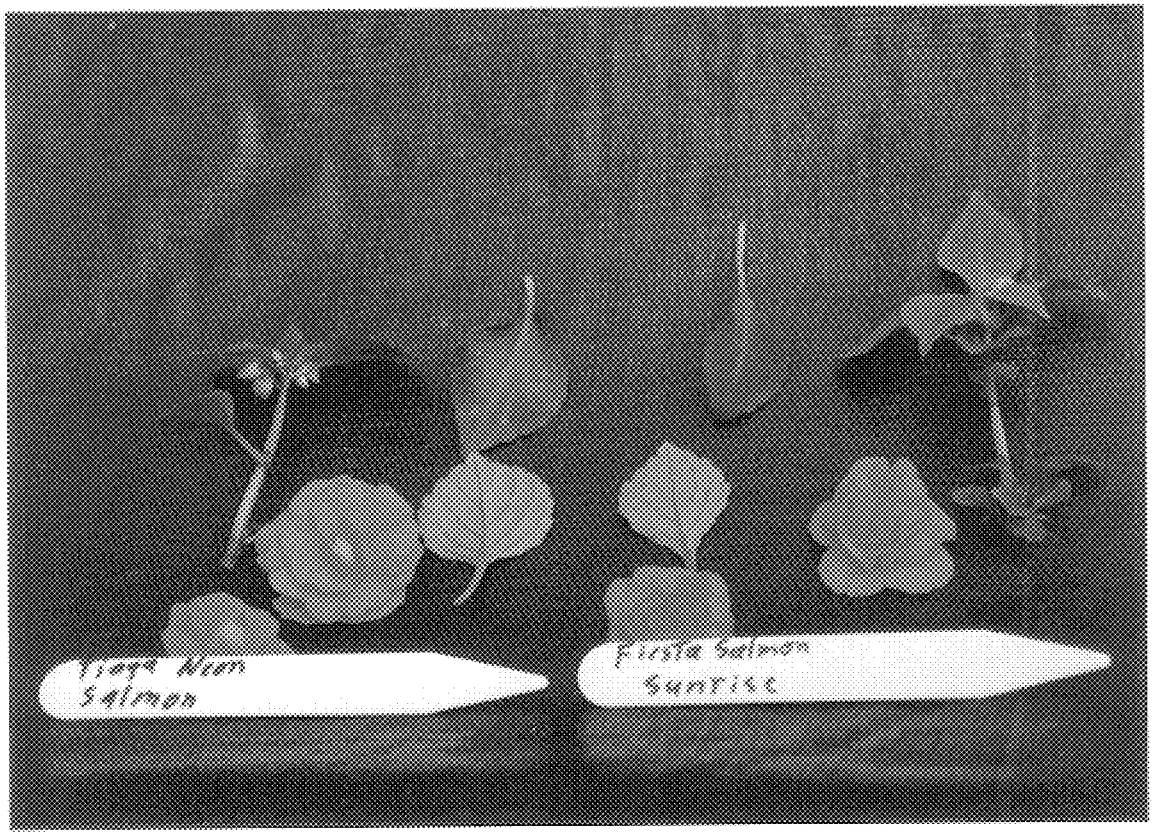
Salmon
Sunrise